United States Patent [19]
West

[11] Patent Number: 5,826,576
[45] Date of Patent: Oct. 27, 1998

[54] ELECTROPHYSIOLOGY CATHETER WITH MULTIFUNCTION WIRE AND METHOD FOR MAKING

[75] Inventor: Scott H. West, Tracy, Calif.

[73] Assignee: Medtronic, Inc., Minneapolis, Minn.

[21] Appl. No.: 694,363

[22] Filed: Aug. 8, 1996

[51] Int. Cl.⁶ ..................................................... A61N 1/05
[52] U.S. Cl. ........................ 128/642; 607/119; 607/122; 604/280
[58] Field of Search ..................................... 128/642, 772; 607/116, 122; 600/146; 604/264, 280, 95

[56] References Cited

U.S. PATENT DOCUMENTS

| | | |
|---|---|---|
| 3,547,103 | 12/1970 | Cook . |
| 4,790,831 | 12/1988 | Skribiski ................................. 604/264 |
| 4,934,340 | 6/1990 | Ebling et al. . |
| 5,255,668 | 10/1993 | Umeda . |
| 5,318,525 | 6/1994 | West et al. . |
| 5,327,905 | 7/1994 | Avitall .................................... 128/642 |
| 5,336,182 | 8/1994 | Lundquist et al. . |
| 5,363,861 | 11/1994 | Edwards et al. . |
| 5,391,147 | 2/1995 | Imran et al. . |
| 5,395,327 | 3/1995 | Lundquist et al. . |
| 5,395,328 | 3/1995 | Lundquist et al. . |
| 5,397,304 | 3/1995 | Truckai . |
| 5,397,321 | 3/1995 | Houser et al. .......................... 607/122 |
| 5,445,148 | 8/1995 | Jaraczewski et al. . |
| 5,487,757 | 1/1996 | Truckai et al. . |
| 5,489,270 | 2/1996 | van Erp . |
| 5,497,782 | 3/1996 | Fugoso . |
| 5,545,200 | 8/1996 | West et al. . |
| 5,556,390 | 9/1996 | Hicks ...................................... 604/280 |

*Primary Examiner*—John P. Lacyk
*Assistant Examiner*—David M. Ruddy
*Attorney, Agent, or Firm*—Townsend and Townsend and Crew LLP

[57] ABSTRACT

An electrophysiology catheter (2) includes a handle (4) and a catheter shaft (6) having a flexible tip portion (22) with one or more electrodes (26, 28). A radial deflection wire (42) connects the tip portion to a first manipulator (10) at the handle to radially deflect the tip portion to a curved shape. A multifunction wire (60) extends from a second manipulator (11) at the handle to the tip portion. The second manipulator slides the multifunction wire longitudinally to position the distal end (64) of the multifunction wire along the multifunction lumen (38). The distal end of the multifunctional wire and the multifunction lumen are configured to provide interfering torquing surfaces (68, 70) so that when a third manipulator (12) rotates or torques the proximal end (62) of the multifunctional wire, the torquing force exerted between the interfering torquing surface causes lateral deflection of the radially curved tip portion. The catheter is constructed so that lateral deflection of the radially deflected tip portion is totally or at least substantially in-plane lateral deflection.

23 Claims, 4 Drawing Sheets

ELECTROPHYSIOLOGY CATHETER WITH MULTIFUNCTION WIRE AND METHOD FOR MAKING

BACKGROUND OF THE INVENTION

Electrophysiology catheters are designed for use in mapping and/or ablation of the heart. Electrophysiology catheters typically include a number of band electrodes mounted to the tip portion of the catheter shaft and a tip electrode at the distal end of the catheter shaft. To properly manipulate the electrodes against the target sites within a heart, the tip portion must be flexible and capable of being manipulated into a variety of shapes. U.S. Patent application Ser. No. 5,487,757, entitled "Multicurved Deflectable Catheter," the disclosure of which is incorporated by reference, discloses an electrophysiology catheter in which the tip portion can be deflected radially by pulling on a manipulator wire and also defected laterally by rotating a core wire which extends into the tip section. In addition to the manipulator and core wires, this patent discloses the use of an axially slidable stiffener wire, the distal end of which can be located at different positions along the tip portion to change the stiffness of the tip, and thus the general size of the curve in the tip.

SUMMARY OF THE INVENTION

The present invention is directed to an electrophysiology catheter which combines the function of a torquable core wire and a slideable stiffener wire into a single element. In addition, the invention provides for the construction of the electrophysiology catheter in a manner so that the lateral deflection can be substantially in-plane lateral deflection.

The electrophysiology catheter includes a handle from which a catheter shaft extends. The catheter shaft has a flexible tip portion carrying one or more electrodes. A radial deflection element, typically a manipulator wire, connects the tip portion to a first manipulator mounted to the handle. Operating the first manipulator causes the tip portion to be deflected or curved radially. A multifunction wire extends from the handle to within the tip portion. The multifunction wire has a distal end which slides within a multifunction lumen formed in the tip portion. This effectively changes the stiffness of the tip portion so to change the general size of the curve in the tip. The multifunction wire is coupled to a second manipulator mounted to the handle. The second manipulator is constructed to allow the user to slide the multifunction wire longitudinally along the catheter shaft so to position the distal end of the multifunction wire at a chosen position along the multifunction lumen within the tip portion. The distal end of the multifunctional wire and the multifunction lumen are configured, that is keyed to one another, to provide interfering torquing surfaces. The user uses a third manipulator to rotate the proximal end of the multifunction wire about its longitudinal axis. This causes the distal end of the multifunction wire to exert a torquing force against the interfering torquing surface of the multifunction lumen, thus causing lateral deflection of the radially curved tip portion.

Another aspect of the invention relates to the ability to maintain the lateral deflection as substantially in-plane lateral deflection. That is, after the tip portion has been deflected radially to its desired curved shape by the manipulator wire, rotating or torquing the multifunction wire preferably results in lateral deflection of the tip portion such that the longitudinal position of the distal end of the tip portion does not change substantially. In-plane lateral deflection can be achieved by one or both of the following. One way is to ensure that the radial curvature of the tip portion is not proximal of the engaged torque-transmitting, interfering torquing surfaces. Because the main portion of the catheter shaft is commonly torsionally stiff, and thus difficult to torque, it is often preferred to limit the longitudinal sliding movement of the multifunction wire so that at its most proximal position, the distal end of the multifunction wire is at least a chosen, minimum distance from the junction of the tip and main portions of the catheter shaft. A second way to achieve in-plane lateral deflection is to ensure that the catheter shaft adjacent to the junction of the tip and main portions of the catheter shaft is torsionally permissive; that is it has low torsional stiffness and is highly torquable or twistable. This can be achieved either by selecting the catheter shaft material at the junction to be highly torquable, by using a rotary joint at the junction, or by other means as well. Using one or both of these approaches, lateral deflection can therefore be totally, or at least substantially, in-plane lateral deflection.

In the preferred embodiment the torque-transmitting distal end of the multifunction wire is sufficiently flexible so it can be bent or flexed radially by pulling or pushing on the manipulator wire; however the remainder of the multifunction wire is preferably stiff enough so not to be bent, to any substantial extent, by pulling or pushing on the manipulator wire. This effectively ensures that the radially-deflected part of the tip portion will not be proximal of the engaged torque-transmitting, interfering torquing surfaces.

Another advantage arises from the fact that only two wires, instead of three wires as in the past, need to be used to obtain the three functions of radial deflection, lateral deflection and change of tip curvature. This permits a larger-diameter manipulator wire to be used because there is more room available for the manipulator wire. The larger diameter manipulator wire has greater columnar strength so to permit the radially-deflected tip portion to be returned to its original, straight shape by pushing on the manipulator wire. This is unlike smaller-diameter, less-stiff manipulator wires which may not have the columnar strength to completely re-straighten the tip portion when the manipulator wire is pushed distally from the handle. This aspect can also permit the tip portion to be deflected in opposite directions depending on whether the manipulator wire is pulled or pushed.

Other features and advantages of the invention will appear from the following description from which the preferred embodiment has been set forth in detail in conjunction with the accompanying drawings.

DESCRIPTION OF THE PREFERRED EMBODIMENT

Figure 1:
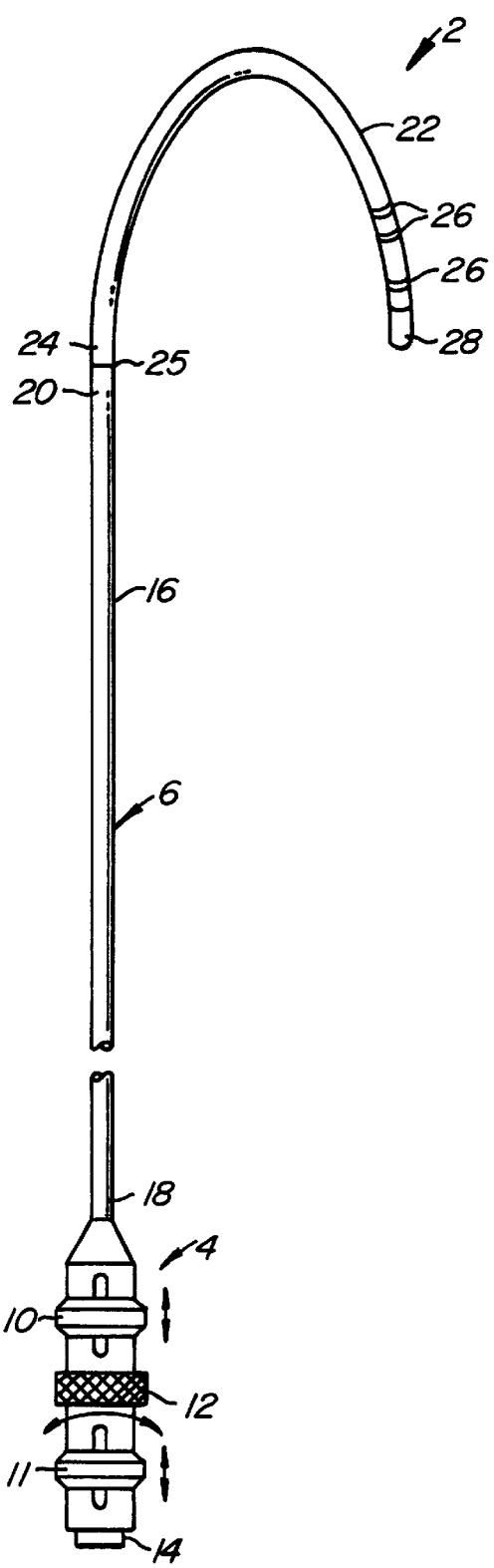
FIG. 1 is a simplified, overall view of an electrophysiology catheter made according to the invention.

FIG. 1 illustrates an electrophysiology catheter 2 including a handle 4 from which a catheter shaft 6 extends. Handle 4 includes a body 8 to which first, second and third manipulators 10, 11 and 12 are movably mounted. Handle 4 also includes an electrical connector 14. Catheter shaft 6 includes a main portion 16, having a proximal end 18 extending from handle 4 and a distal end 20. Catheter shaft 6 also includes a tip portion 22 having a proximal end 24 affixed to and extending from distal end 20 of main portion 16 at a butt joint 25. Tip portion 22 has a number of band electrodes 26 and a tip electrode 28, the tip electrode 28 being at the distal end of tip portion 22.

Figure 2A:
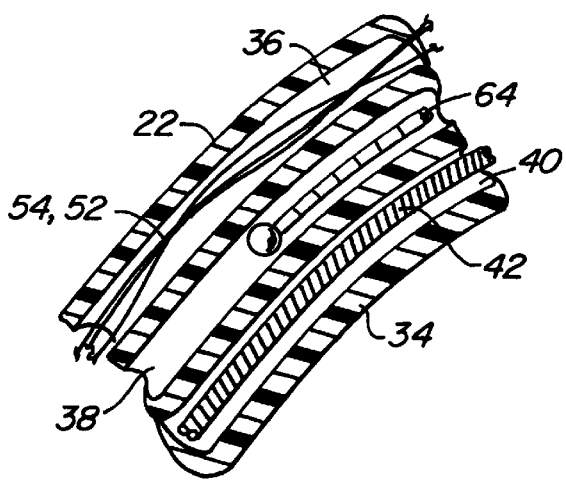
FIGS. 2A and 2B are enlarged, detailed cross-sectional views of the tip portion of FIG. 2 taken at the distal end of the multifunction wire and the distal end of the tip portion, respectively.
Figure 2B:
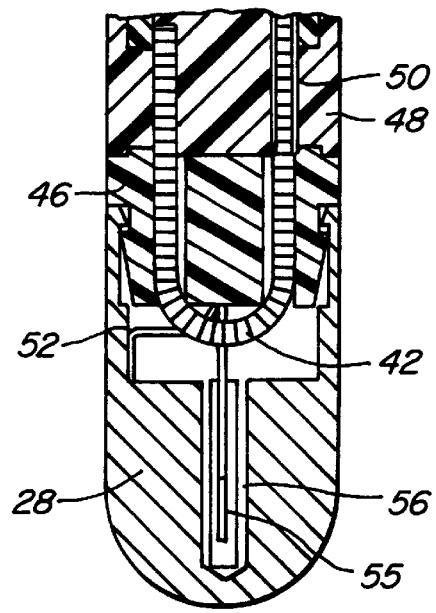
Figure 2:
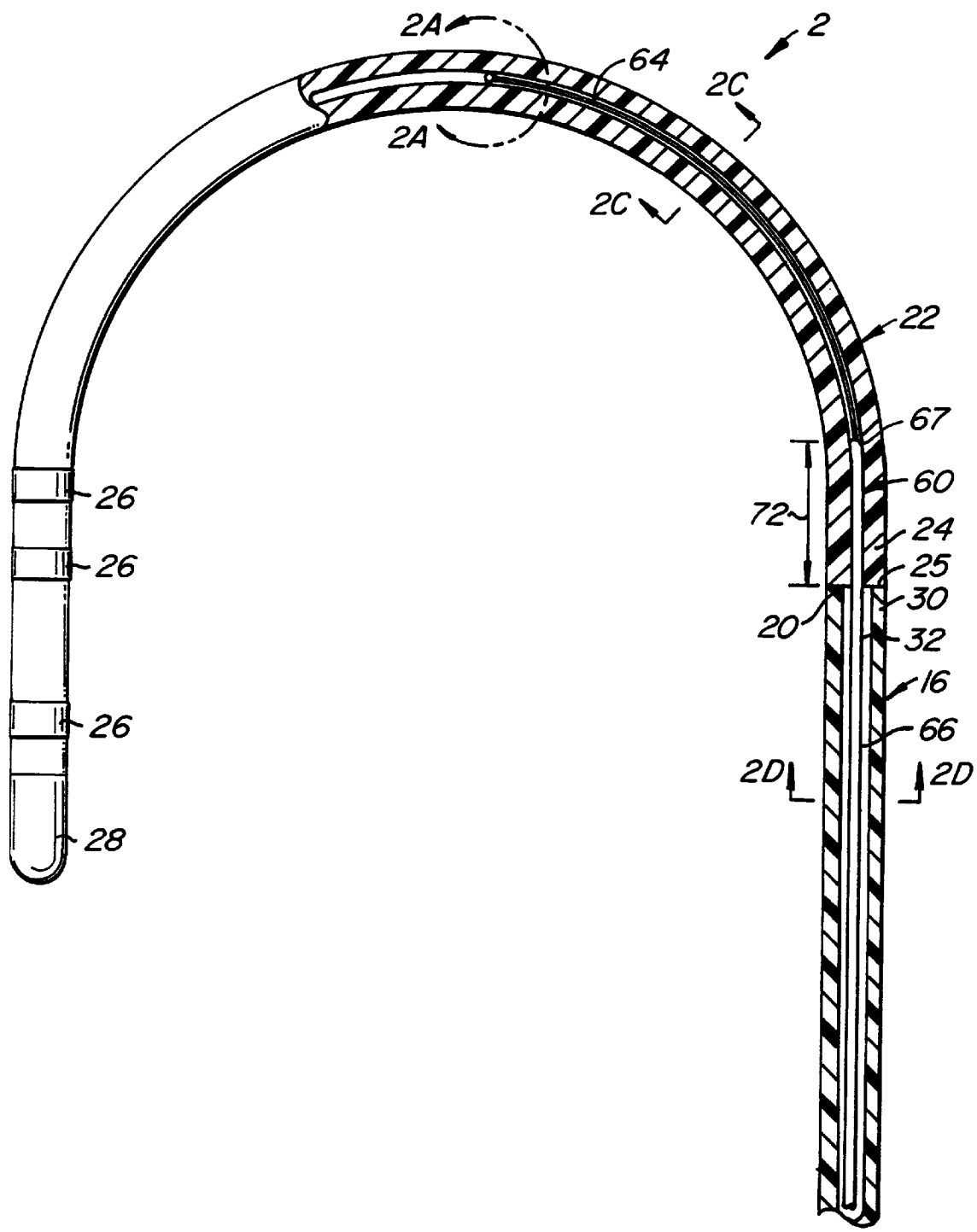
FIG. 2 is an enlarged, simplified partial cross-sectional view of the tip portion of the catheter shaft of FIG. 1 illustrating the multifunction wire in a more proximal position providing a larger radial deflection curve.
Figure 2C:
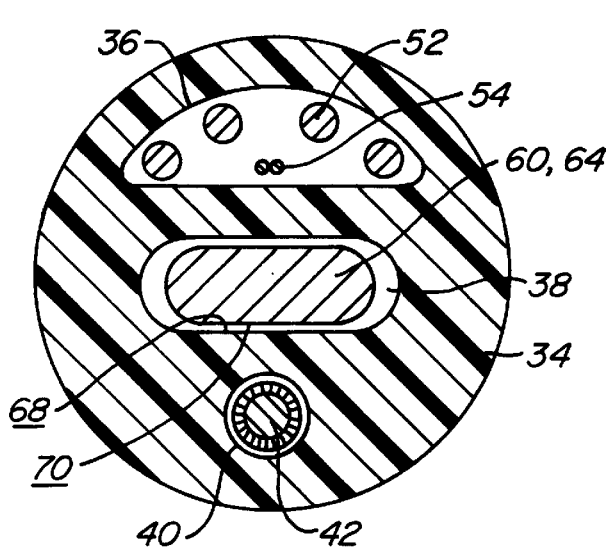
FIG. 2C is a cross-sectional view taken along line 2C—2C of FIG. 2 illustrating three lumens formed in the tip portion body and illustrating the interfering torquing surfaces of the distal end of the multifunction wire and the multifunction lumen, both having similar oblong cross-sectional shapes.
Figure 2D:
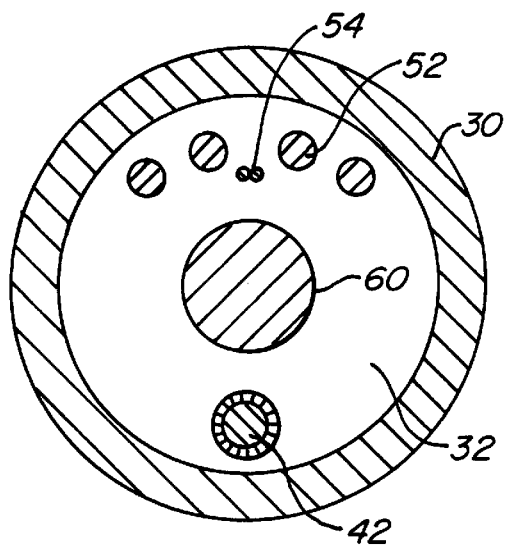
FIG. 2d is a cross-sectional view taken along line 2D—2D of FIG. 2 illustrating a proximal portion of the multifunctional element and a manipulation wire.

Referring now also to FIGS. 2–2D, main portion 16 of catheter shaft 6 is seen to comprise a reinforced shaft body 30 defining a main lumen 32. Body 30 is preferably made of a polyetherimide inner liner, a stainless steel wire braid and a PEBAX® (polyamide polyether block copolymer) outer jacket. The PEBAX outer jacket has a Durometer hardness reading of about 40D–-75D, and preferably about 55D. Main portion 16 is stiffer than tip portion 22 and, if desired, can be made to be stiffer closer to proximal end 18 than distal end 20. Tip portion 14 includes a tip portion body 34 having, in this embodiment, three axially extending lumens, specifically electrical wire lumen 36, multifunction wire lumen 38, and radial deflection wire lumen 40. Body 34 is preferably made of PEBAX and has a Durometer hardness reading of about 35D–55D, and more preferably about 40D. A radial deflection wire 42, typically made of PTFE-coated stainless steel, extends from first manipulator 10 at its proximal end to an insulating connector 46 adjacent to tip electrode 28. Wire 42 has a diameter of about 0.015 inch along most of its length but preferably tapers to a smaller diameter, such as about 0.009 inch, at its distal end. Insulating connector 46 is preferably made of PEEK, or another hard insulating material, and is thermally or otherwise bonded to the distal end 48 of tip portion body 34.

In the preferred embodiment the section of tip portion 22 carrying electrodes 26, 28 is preferably stiffer than the remainder of tip portion 22 to create a straight section at the distal end; such section of tip portion 22 could be more stiff or less stiff than the remainder of the tip portion depending upon the particular characteristics desired. To provide this additional stiffness, a hypotube 50, made of stainless steel, is positioned over radial deflection wire 42 between insulating connector 46 and the most proximal band electrode 26.

Electrical wires 52 extend from electrical connector 14 of handle 4, through main lumen 32 in reinforced shaft body 30, through electrical wire lumen 36 in tip portion body 34 and terminate at the various electrodes 26, 28. Thermocouple wires 54, like electrical wires 52, pass from electrical connector 14, through handle 4, along lumens 32, 36 and terminate to form a thermocouple 55 housed within a cavity 56 formed in tip electrode 28. Thermocouple 55 is surrounded by a thermally-conducting, electrically-insulating material, such as LOCTITE 498 cyanoacrylate thermal cycling adhesive. Wires 52 are preferably insulated nickel wires.

Figure 3:
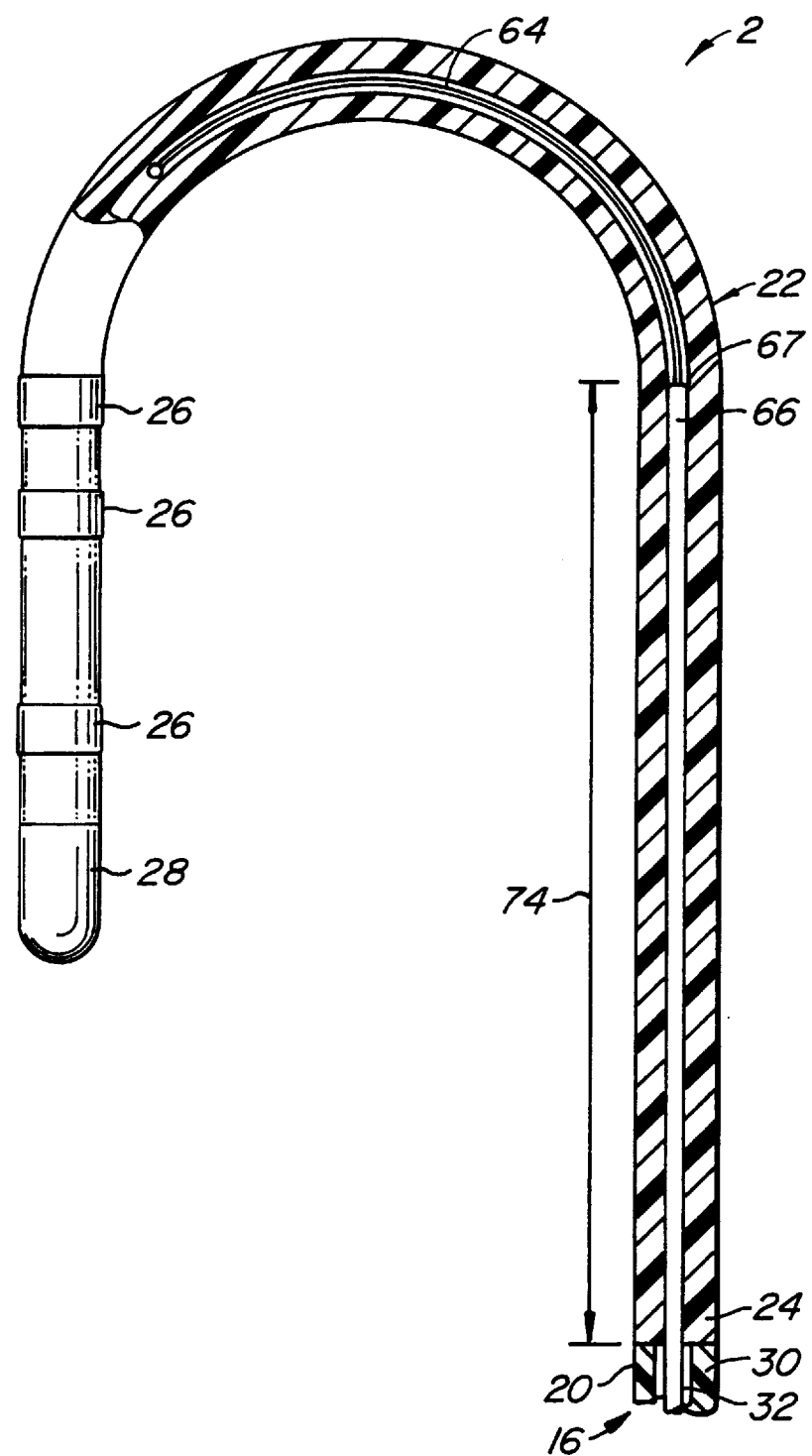
FIG. 3 illustrates the tip portion of FIG. 2 with the distal end of the multifunction wire moved in a distal direction relative to the position of FIG. 2 causing the tip portion to be stiffer, thus creating a smaller radius curve in the tip portion upon actuation of the radial deflection wire.

A multifunction wire 60, shown in FIGS. 2 and 3, has a proximal end coupled to second manipulator 11 of handle 4 and a distal end 64. Distal end 64 is about 20–40 mm and preferably 30 mm long, and has an oblong cross-sectional shape as seen best in FIG. 2C. Distal end 64 has cross-sectional dimensions of about 0.002 to 0.005 inch, and preferably about 0.003 inch, by 0.030 to 0.050 inch, and preferably about 0.040 inch. The remainder 66 of multifunction wire 60 has a generally circular cross-sectional shape of about 0.015 to 0.025 inch, and preferably about 0.020 inch, diameter. Both distal end 64 and remainder 66 are sized to pass through multifunction wire lumen 38 which also has an oblong cross-sectional shape, preferably about 0.020 inch by 0.050 inch. Wire 60 can have different cross-sectional shapes and can be made of stainless steel, nickel titanium, plastic or other materials which provide sufficient flexibility and torsional stiffness. Wire 60 is preferably coated with PTFE or some other low-friction material.

The longitudinal movement of second manipulator 11 causes the like longitudinal movement of multifunction wire 60 to move distal end 64 between a more proximal position of FIG. 2 and a more distal position of FIG. 3. In the position of FIG. 2, tip portion 14 is not as stiff along its entire length as when in the position of FIG. 3. Thus pulling, or pushing, on radial deflection wire 42 by the manipulation of first manipulator 10 causes tip portion 22 to assume a larger radius curved shape as shown in FIG. 2 or a smaller radius curved shape as shown in FIG. 3. In the preferred embodiment remainder 66 of multifunction wire 60 is sufficiently stiff so that substantially all radial deflection of tip portion 14 occurs distal of the junction 67 of distal end 64 and remainder 66.

Radially deflected tip portion 14 can be deflected laterally by rotating or torquing the proximal end of multifunction wire 60 through the rotation of third manipulator 12. The section of multifunction wire 60 which slides longitudinally through third manipulator 12 (due to the longitudinal movement of second manipulator 11) has an other-than-round cross-sectional shape, such as a dumbbell-shape, which fits within a generally complementary hole in the third manipulator. This arrangement permits the user to torque the proximal end of the multifunction wire by rotating third manipulator 12 about the handle axis. The lateral deflection of tip portion 14 occurs because of the respective shapes of multifunction wire lumen 38 and distal end 64 of multifunction wire 60. That is, lumen 38 and distal end 64 have torque-transmitting, interfering torquing surfaces 68, 70 which engage on the rotation or torquing of multifunction wire 60. Tip portion body 34 is sufficiently twistable/torquable (as opposed to shaft body 30) so that the twisting or torquing of catheter shaft 6 occurs along the length of the tip portion proximal of distal end 64 of multifunction wire 60. This length is indicated by distances 72 and 74 in FIGS. 2 and 3, respectively.

The circular cross-sectional shape of remainder 66 of multifunction wire 60 is generally preferred because of its torsional stiffness. The oblong cross-sectional shape of distal end 64 can be changed to other shapes, such as cruciform, so long as distal end 64 and multifunction wire lumen 38 have interfering torquing surfaces. While distal end 64 and lumen 38 will typically have similar cross-sectional shapes, they need not. For example, distal end 64 could have an oblong cross-sectional shape while lumen 38 could have a cruciform cross-sectional shape sized to provide interfering torquing surfaces with distal end 64. Other shapes, including shapes with curved interfering torquing surfaces, which key to one another could also be used. While multifunction wire 60 can be a one-piece wire, it is preferably made by welding distal end 64 and remainder 66 at junction 67.

Figure 4:
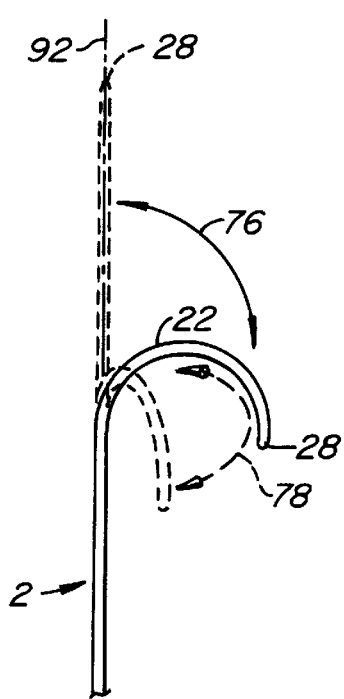
FIG. 4 is a schematic illustration showing in-plane lateral deflection of a radially deflected catheter tip portion.
Figure 5:
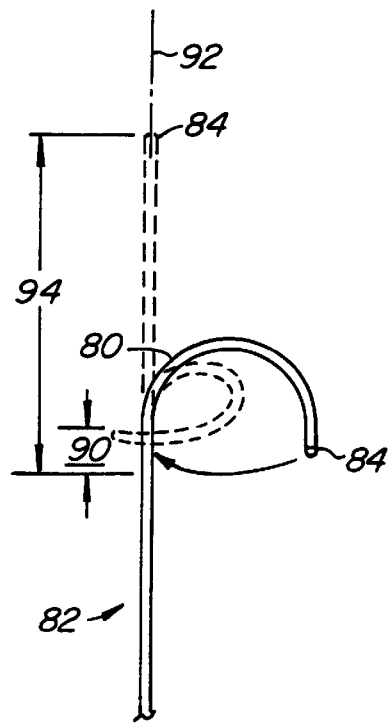
FIG. 5 is a schematic illustration showing out-of-plane lateral deflection of a radially deflected catheter tip portion.

So long as this twistable/torquable portion 72, 74 is substantially straight, lateral deflection of curved tip portion 22 will not change the shape of curved tip portion 22. As a result, such lateral deflection of tip portion 22 is said to be in-plane lateral deflection. In-plane lateral deflection is illustrated in FIG. 4 with the radial deflection indicated by arrow 76 and the in-plane lateral deflection, in which the shape of tip portion does not change, is indicated by arrow 78. This is in contrast with the out-of-plane lateral deflection of conventional torquable electrophysiology catheters in which the lateral deflection force is exerted near the distal end of the tip portion of the catheter. Out-of-plane lateral deflection of the prior art, shown in FIG. 5, typically results from when the shape of the tip portion 80 of a catheter 82 is changed by the lateral deflection of the tip portion in a corkscrewing type of manner. That is, during out-of-plane lateral deflection, the distal end 84 of tip portion 80 moves laterally in a rotary direction and also axially in a distal direction.

In the preferred embodiment the torsional stiffness of tip portion body 34 is basically uniform along its entire length. However, if desired a part of tip portion 14 adjacent to proximal end 24 can be made to have a lower torsional stiffness than the remainder of tip portion 14. Doing so helps to ensure that any curved tip portion 14 proximal of junction 67 does not torque to any substantial extent but rather the entire, or at least substantially the entire, torsion of tip portion 14 occurs adjacent butt joint 25. This also helps to ensure that the lateral deflection of tip portion 14 is substantially in-plane lateral deflection since the part of tip portion 14 adjacent to butt joint 25 preferably remains straight during use. Instead of using a low torsional stiffness part adjacent butt joint 25, the same effect can be achieved using a rotational coupling at butt joint 25.

When constructing electrophysiology catheter 2 it is preferred that movement of multifunction wire 60 be limited so that the minimum distance 72 between distal end 64 of multifunction wire 60 and proximal end 24 of tip portion 22 is at least about 0.400 to 0.800 inch, and preferably about 0.600 inch. This limits the amount of torquing force required and helps to ensure that lateral deflection of tip portion 22 occurs without substantially changing the shape of the curved tip portion during lateral deflection of at least 90° in each direction. Maintaining the shape of the radially deflected tip portion 22 ensures that the lateral deflection of tip portion 22 is substantially in-plane lateral deflection.

As used in this application, substantially in-plane lateral deflection exists when any change 90 in the axial position of distal end 84 of tip portion 80, as measured parallel to axis 92, for 90° of lateral deflection is less than about 10% of the initial deflection 94 of distal end 84.

In use, catheter shaft 6 is translumenly positioned through a blood vessel within a patient so that flexible, deflectable tip portion 22 is within the heart. Second manipulator 11 is moved longitudinally to position distal end 64 of multifunction wire 60 at the appropriate position within multifunction wire lumen 38 according to the size of the radial curve desired. An axial force is then applied by the manipulation of first manipulator 10 pulling on or pushing radial deflection wire 42 to cause tip portion 22 to move into a radial curve. Third manipulator 12 is then manipulated to rotate the proximal end of multifunction wire 60 thus causing the engagement of surfaces 68, 70 and the lateral deflection of tip portion 22. These various manipulations are done to allow the physician to properly position electrodes 26, 28 at the appropriate target site. If desired, these steps can be done in different order or one or more steps may be omitted or deleted. Mapping, ablation, or other procedures can then be accomplished through electrical connector 14, electrical wires 52 and electrodes 26, 28.

Modification and variation can be made to the disclosed embodiment without departing from the subject of the invention as defined in the following claims. For example, it may be possible to combine the functions of second and third manipulators 11, 12 into a single manipulator which provides the functions of both.

What is claimed is:

1. An electrophysiology catheter comprising:
   a handle comprising first, second and third manipulators;
   a hollow, flexible catheter shaft extending from the handle;
   the catheter shaft comprising a main portion having a distal end and a tip portion, the tip portion comprising a proximal end adjacent the main portion distal end and a distal end;
   an electrode carried by the tip portion;
   an electrical conductor extending through the catheter shaft from the electrode to the handle;
   a multifunction element extending along the catheter shaft, said multifunction element having a proximal end and a distal end, wherein the multifunction element proximal end is operably coupled to the second and third manipulators;
   said second manipulator constructed to selectively slide said multifunction element longitudinally, so to position said multifunction element distal end at a chosen location;
   said third manipulator constructed to selectively torque the multifunction element proximal end;
   a radial deflection element having a proximal end, terminating at the handle and operably coupled to the first manipulator, and a distal end, connected to a position along the tip portion, so that actuation of the first manipulator causing longitudinal movement of the radial deflection element causes radial deflection of the tip portion distal end;
   said multifunction element having a stiffness which changes the radial bending curvature of the catheter depending on the chosen location of the multifunction element, so that the shape of said radial deflection is affected by said chosen location of said multifunction element distal end;
   said tip portion comprising a lateral deflection lumen housing said multifunction element distal end for longitudinal sliding movement therein;
   said lateral deflection lumen and said multifunction element distal end comprising interfering torquing surfaces so that torquing said multifunction element by said third manipulator causes said interfering torquing surfaces to engage and causes lateral deflection of said tip portion distal end.

2. The catheter according to claim 1 wherein said electrode comprises a tip electrode and a plurality of band electrodes.

3. The catheter according to claim 1 wherein said main portion of said catheter shaft comprises a braided shaft.

4. The catheter according to claim 1 wherein the tip portion of said catheter shaft comprises an unreinforced tube defining a plurality of axially extending lumens.

5. The catheter according to claim 4 wherein said tip portion of the catheter shaft has Durometer hardness reading in the range of 35D to 55D.

6. The catheter according to claim 5 wherein said Durometer hardness reading of about 40D.

7. The catheter according to claim 1 wherein the interfering torquing surfaces comprise flat surfaces.

8. The catheter according to claim 1 wherein said lateral deflection lumen has an oblong cross-sectional shape.

9. The catheter according to claim 8 wherein said multifunction distal end has an oblong cross-sectional shape.

10. The catheter according to claim 1 wherein said handle comprising an electrical connector to which the electrical conductor is connected.

11. The catheter according to claim 1 wherein said radial deflection element comprises a manipulator wire connected to the distal end of the tip portion.

12. The catheter according to claim 1 wherein said radial deflection element is configured to deflect the tip portion radially both when the radial deflection element is placed in tension and in compression.

13. The catheter according to claim 1 wherein said position along the portion is at the distal end of the tip portion.

14. The catheter according to claim 1 wherein said multifunction element other than said multifunction distal end has a circular cross-section shape.

15. The catheter according to claim 14 wherein said multifunction distal end has an oblong cross-sectional shape.

16. The catheter according to claim 15 wherein said oblong cross-sectional shape is an oval cross-sectional shape.

17. The catheter according to claim 15 wherein said main portion has a diameter of about 0.015 to 0.025 inch, and said distal portion has a maximum cross-sectional dimension of about 0.030 to 0.050 inch and a minimum cross-sectional dimension of about 0.002 to 0.005 inch.

18. The catheter according to claim 17 wherein said diameter is about 0.020 inch, said maximum cross-sectional dimension is about 0.040 inch, and said minimum cross-sectional dimension is about 0.003 inch.

19. The catheter according to claim 1 wherein the multifunction element comprises said distal end and a remainder portion, said distal end being affixed to said remainder portion.

20. An improved electrophysiology catheter of the type comprising a handle including a manipulator, a catheter shaft extending from the handle and having a flexible tip portion, an electrode mounted to the tip portion and electrically coupled to the handle, and a radial deflection element, coupled to manipulator at one end and the flexible tip portion at the other end, capable of radially deflecting the tip portion to a radially curved shape, the improvement comprising:

the handle comprising a second and third manipulator;

a multifunction element, extending along the catheter shaft, having a proximal end operably coupled to the second and third manipulators and a distal end housed within the tip portion;

said second manipulator constructed to cause the multifunction element to slide longitudinally, so to position the multifunction element distal end at a chosen longitudinal location along the tip portion;

said third manipulator constructed to torque the multifunction element proximal end;

said multifunction element having a stiffness which changes the radially curved shape of the catheter depending on the chosen location of the multifunction element;

said tip portion comprising a lateral deflection lumen housing said multifunction element distal end for longitudinal sliding movement therein;

said lateral deflection lumen and said multifunction element distal end comprising interfering torquing surfaces so that torquing said multifunction element by said second manipulator causes said interfering torquing surfaces to engage and causes lateral deflection of said tip portion distal end.

21. A catheter comprising:

a catheter shaft having a tip portion, said tip portion defining a first lumen;

a multifunction element extending along the catheter shaft and having a distal portion extending into and freely longitudinally slidable within said first lumen;

said multifunction element constructed to selectively slide longitudinally to a chosen location;

said multifunction element having a stiffness which changes a radial bending curvature of the catheter depending on the chosen location of the multifunction element; and the lumen and distal portion having interfering torquing surfaces so that rotating the multifunction element torques the tip portion.

22. The catheter according to claim 21 further comprising a radial deflection element extending along the catheter shaft and having a distal end secured to the tip portion to permit the tip portion to be deflected radially.

23. The catheter according to claim 22 wherein the distal portion comprises a second lumen housing said distal end.

* * * * *